United States Patent [19]

Petersen

[11] Patent Number: 4,826,495
[45] Date of Patent: May 2, 1989

[54] COUPLING MEANS FOR FASTENING DISPOSABLE OSTOMY BAGS AND BAG SYSTEM THEREFORE

[75] Inventor: Morten L. Petersen, Helsingor, Denmark

[73] Assignee: Coloplast A/S, Espergaerde, Denmark

[21] Appl. No.: 85,734

[22] Filed: Aug. 17, 1987

[30] Foreign Application Priority Data

Sep. 4, 1986 [DK] Denmark ............................. 4223/86

[51] Int. Cl.⁴ .............................................. A61F 5/441
[52] U.S. Cl. ..................................... 604/333; 604/344
[58] Field of Search ................................ 604/333, 344

[56] References Cited

FOREIGN PATENT DOCUMENTS

| 77392 | 4/1954 | Denmark | 604/333 |
| 496203 | 10/1950 | France | 604/333 |
| 648718 | 1/1951 | United Kingdom | 604/333 |
| 1295252 | 11/1972 | United Kingdom | 604/333 |

*Primary Examiner*—Albert W. Davis, Jr.
*Attorney, Agent, or Firm*—Armstrong, Nikaido, Marmelstein Kubovcik & Murray

[57] ABSTRACT

In a re-usable coupling means for securing flexible disposable bags for collecting intestinal wastes from ostomies and which consists (a) of a retainer plate of a comparatively stiff plastic material having an opening to lie around the stoma and having a gas passage duct communicating with a deodorizing filter, and (b) a flexible, sealing adhesive member for releasable adherence of the retainer plate to the skin and indirectly secured to the rear of the retainer plate, the gas passage duct is arranged in an annular bead protruding from the front of the retainer plate and communicates via gas inlet openings with the interior of the bag and via the filter and gas outlet openings in the coupling means with the outer world. The disposable bag may be releasably affixed to the holding means by the aid of a pressure-sensitive adhesive or by the aid of ring coupling systems known per se. This coupling means is particularly well suited for use in ostomy bag systems of the kind consisting of a wc-flushable inner bag of a laminated sheet material with an outer layer of water-soluble film and a water- and gas-proof, mechanically weak inner layer; and an outer reusable bag of a water-tight, mechanically strong material.

8 Claims, 4 Drawing Sheets

COUPLING MEANS FOR FASTENING DISPOSABLE OSTOMY BAGS AND BAG SYSTEM THEREFORE

Field of the Invention

The present invention relates to a re-usable coupling means for fastening a flexible disposable ostomy bag to the abdominal wall of an ostomy patient.

This coupling means is constituted by (a) a retainer plate of a comparatively stiff plastic material, provided with an opening adapted to surround the stoma when the coupling means is positioned around it and having a gas passage duct connected to a filter for deodorizing flatus, and (b) a flexible sealing adhesive member adapted to releasably adhering the retainer plate to the skin around the stoma and being permanently connected with the rear of the retainer plate.

BACKGROUND OF THE INVENTION

Many constructions of ostomy bags are known and many of them are secured to the patient by means of special carrying, holding or coupling means. It is also well-known to provide ostomy bags in some manner or other with filters to deodorize flatus. Such filters may be built into the bag or they may be separate and adapted to be placed over a permanent opening in the bag or one formed for the occasion. In the former case the filter is always discarded together with the bag, in the latter the same is often the case but not always.

Many different holding or coupling means for affixing to the skin of the patient are known, e.g. by adhesion or by the aid of a belt, and many of them are. adapted to releasably receive an ostomy bag, e.g. by means of suitable coupling rings or other coupling elements, or adhesively. Such holding or coupling means as a rule may be used several times, which firstly is an economic advantage because such a means is a comparatively costly element in the overall ostomy bag arrangement, and secondly because thereby they can remain in place on the skin of the patient around the stoma for a comparatively long period of time, which is advantageous because the replacement of the holding means frequently may cause discomfort or even pain.

The filter is also a comparatively expensive part of the ostomy bag arrangement and it is therefore advantageous to build it into the holding or coupling means.

A few examples of doing this are known. Thus, GB patent specification No. 1,595,906 describes a surgical dressing having a carrier pad one side of which can adhere to the skin of the patient and the other side of which is provided with a first coupling member whereby a colostomy bag can be secured to the pad by means of a second coupling member secured to the bag, all provided with apertures which can be aligned with the stoma to allow intestinal contents to flow into the bag. The specific feature of this dressing is that a gas passage path extends through the pad or the first coupling member to the outer world, all of the gas passage path extending substantially vertically upwardly when the pad is being worn normally by an upright patient, the portion of the gas path placed in the pad or the first coupling member having a gas filter inserted. The gas filter is, as nearly always and also according to the present invention, based on activated carbon.

A similar construction is known from U.S. Pat. No. 4,232,672. Although it is not said in the claims of that patent that a filter compartment has to turn upwardly during use, this is clear from the description. The main difference relative to the above-mentioned GB patent is that one or more ducts lead from the interior of the bag to the filter compartment and that these ducts may be closed by a valve arrangement which via a resilient member is connected to a push button; only when this is activated, flatus will escape from the bag. From GB patent specification No. 1,212,904 there is also known a holding means for ostomy bags, this means provided with a flatus discharge duct which may be closed by a valve. In this case there is no gas filter in the duct.

It is a disadvantage of the known constructions mentioned that they need to have the holding or coupling means situated at the skin of the patient at a definite orientation, firstly because this may be difficult, secondly because the vertical orientation only exists when the patient is standing or walking, but not when he is lying, especially not when he is lying on his side. It is advantageous to be able to close the gas discharge duct when is does not contain a gas filter, but otherwise it is comparatively unimportant or even a disadvantage (if one forgets the venting, the bag will be inflated by flatus), and in both cases the valve arrangement is relatively complicated and at any rate it will increase the cost.

BRIEF DESCRIPTION OF THE INVENTION

It is the object of the invention to eliminate these drawbacks and according to the invention this is achieved by having the gas passage duct situated in an annular projection protruding from the front of the retainer plate around the opening, said duct (when the bag has been positioned correctly on the coupling means) communicating at one hand with the interior of the bag by a plurality of gas inlet openings and at the other hand via the filter with one or more gas outlet openings in the coupling means.

It is thereby obtained that no matter the position of the wearer, be it standing, sitting or lying, and irrespective of the position of the coupling means relative to the bag, the filter will always be active to deodorize flatus, which will in any event be able to penetrate to and through the filter whenever flatus passes from the intestine into the bag. Flatus flows into the duct, via the filter to the outer world in consequence of the gas pressure it exerts and it is not a necessity for flatus to pass upwardly through the retainer plate.

In the present specification the front and rear of the retainer plate and other parts consistently mean the sides which during use are turned away from and toward, respectively, the person wearing the bag or its accessories. Upper and lower parts of bags and other constructional elements discussed herein are those which are upper and lower, respectively, when the bag etc. is positioned correctly on an upright person.

DETAILED DESCRIPTION OF THE INVENTION

Apart from what has been mentioned above, the coupling or fastening means according to the invention has a further advantage, viz. that it can be used *not only* for ordinary ostomy bags but also for that known kind of wc-flushable disposable bags with a water-soluble outer layer which are adapted to be placed, as the inner bag, in a mechanically strong outer bag for use several times and protecting the inner bag from coming into contact with water.

In cases where it is wanted to benefit from this property, the gas outlet opening from the filter should be preferably situated in the rear of the retainer plate whereas the front of the retainer plate in an area surrounding the annular protection should be adapted to hold the bag by the aid of a pressure-sensitive adhesive. This will normally in known manner be covered by a removable protective cover until use. The pressure-sensitive adhesive may be present at the said area of the retainer plate or/and at a corresponding area on the bag.

Although, seen from the production point of view, it is simplest to have the gas discharge opening from the filter debouch in the rear of the retainer plate (i.e. in use between the bag/retainer plate and the body of the wearer), nothing prevents that it debouches in the outside edge of the retainer plate.

It goes without saying that it is also possible to construct the coupling means in such a manner that the annular projection together with the retainer plate constitutes one part of a releasable ring coupling (a so-called plate coupling) the other ring coupling part of which (a, so-called bag coupling) is adapted to co-operate therewith and is firmly connected to the bag. Many different constructions of such ring couplings are known and they do not per se constitute any part of the present invention. A suitable embodiment is described in U.S. patent application Ser. No. 867,523, the relevant part of this is hereby incorporated herein.

Because of, i.a., the relative easiness at which it may be produced, a particularly advantageous embodiment of the coupling means according to the present invention is constructed as follows:

(i) the gas passage duct is closed to the rear of the retainer plate and situated in a bead protruding from the front of the retainer plate, said bead radially inwardly delimiting the opening of the retainer plate and radially outwardly an area for receiving an area of the disposable bag provided with a pressure-sensitive adhesive, (ii) the gas passage duct is in communication by means of a plurality of gas inlet openings, distributed evenly over the perimeter of the bead, with the interior of the disposable bag when it is positioned correctly on the retainer plate, and (iii) the filter is placed adjacent the rear of the retainer plate such that an inlet opening for gas to flow to the active filter material communicates via a small chamber with the gas passage duct, and also such that gas can only flow from the duct through this inlet opening and the active filter material, whereas a discharge path for the gas from the active filter material debouches opposite a part of the adhesive member not secured to the retainer plate.

The filter may advantageously be of the kind disclosed in EP patent application No. 871 300747.0 and may have been inserted in a recess from the rear of the retainer plate, said recess being barred from the rear of the retainer plate, but communicating with the gas passage duct.

The invention also relates to a disposable bag adapted for use together with a coupling means constructed as disclosed above, which bag has an entrance opening for intestinal wastes and around that an area provided with a pressure-sensitive adhesive for affixing at the front of the retainer plate defined, said adhesive area being provided with a bipartite protective cover before the bag is being taken into use. Such a bipartite cover is known, from FIG. 1 of GB Pat. No. 2,094,153; for reasons of easy production the dividing line is always eccentric, a chord not intersecting the entrance opening to the bag. According to the present invention it should be diametrical relative to said entrance opening and horizontal when worn by an upright patient. In the present context, i.e. for use with a reusable retainer plate and especially for use as inner bag in the system described hereinbelow, this positioning of the dividing line between the parts of the protective cover greatly facilitates the replacement of bags on the retainer plate when the latter is in place on a patient.

Particularly expediently the bag may be of the known wc-flushable kind consisting of a laminated sheet material of which the outer layer consists of a water-soluble film whereas the inner layer is water and gas-tight, but mechanically weak and disintegrable in turbulent water.

The invention also relates to an ostomy bag system comprising a coupling means as described, a wc-flushable bag preferably of said kind, and a bag of a waterproof, mechanically strong material, the latter bag meant for use several times and adapted to be placed as an outer bag around the wc-flushable bag serving as inner bag. In this the rear wall of the outer bag is bipartite in such a manner that its lower portion extends to a level which in the use position borders on the lower part of the area of affixing the sealing adhesive member at the retainer plate, whereas its upper portion is a plate-like portion which has a recess extending from its lowermost edge and having a contour in its upper part adapted to engage the upper half of the gap between the retainer plate and the sealing adhesive member secured thereto, said recess at both sides being delimited by flaps overlapping the lower portion of the rear wall.

In such an ostomy bag system, the flaps on the upper portion of the rear wall of the outer bag and/or the lower portion of the rear wall is provided with means for releasably locking the two portions of the rear wall together. These means may have the form of areas with a pressure sensitive adhesive on one of the portions but may e.g., also be a Velcro type locking means (i.e. hooks at one part engaging loops on the other) or a snap fastener system.

BRIEF DESCRIPTION OF THE DRAWINGS

In the following the invention will be explained more detailedly with reference to the drawings. In the drawings

DETAILED DESCRIPTION OF PREFERRED EMBODIMENTS

Figure 1:
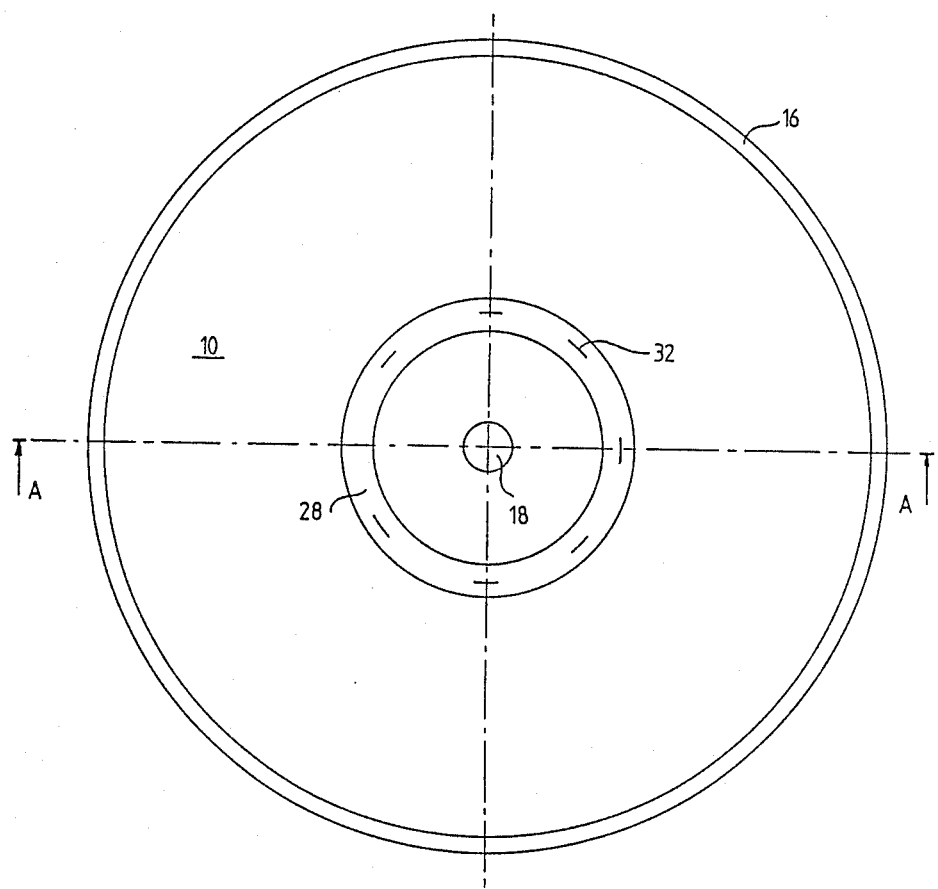
FIG. 1 shows a plan view of an embodiment of a coupling means according to the invention.
Figure 2:
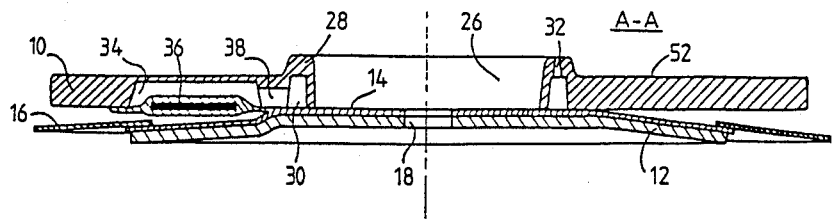
FIGS. 2 and 3 show sections along the line A-A in FIG. 1 of two slightly different embodiments of the coupling means.
Figure 3:
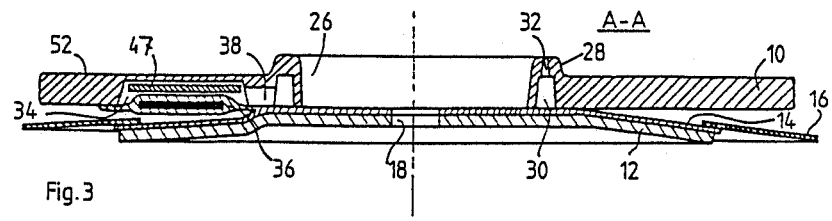

The holding means shown in FIGS. 1–3 mainly consists of a retainer plate 10 of a comparatively stiff plastic material, for instance having a thickness of 1–2 mm; and a skin-friendly adhesive and sealing pad 12, e.g. of a material as described in GB patent specifications Nos. 1576522 and 2089351. The adhesive and sealing pad 12 in the embodiments shown in FIGS. 2–3 is connected to the retainer plate 10 via a thin layer of plastic film 14 (not shown in FIG. 5) which also serves at securing a thin microporous tape 16 which in a known way serves at fastening the coupling means safely to the skin.

Figure 5:
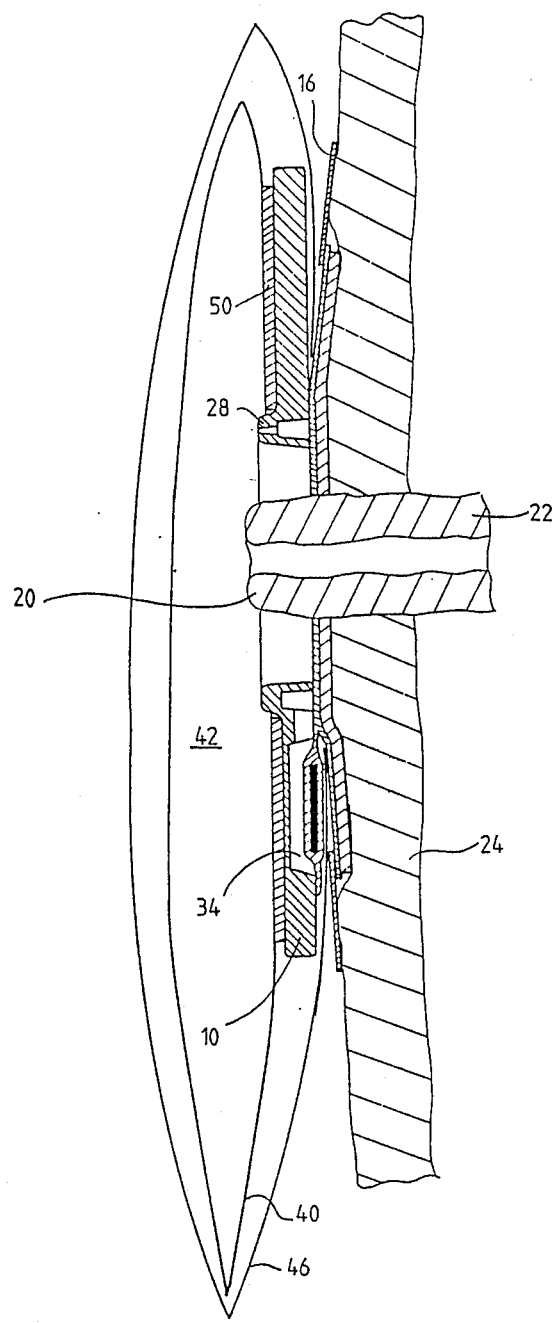
FIG. 5 shows schematically in slightly larger scale than FIG. 4 a section of a bag system according to the invention, consisting of a coupling system as shown in FIGS. 1-3, a wc-flushable inner bag and an outer bag, attached to the skin around a stoma.

In the middle of the interconnected (e.g. by heat sealing) two layers, i.e. the plastic film and the adhesive and sealing pad, there is an aperture 18 which does not need to be present at manufacturing because it is intended to be adapted in known manner by the patient or the nursing personnel so as to suit and fit tightly around a stoma 20 (which usually protrudes from the abdominal wall; see FIG. 5 in which reference numeral 22 visualizes the intestinal wall partly turned inside out and 24 the abdominal wall).

There is also a central opening 26 in the retainer plate 10, and the stoma may protrude more or less into or through it. The opening 26 has a larger diameter than the outer diameter of the stoma, viz. to ensure that the adhesive and sealing pad 12 may bear against the outside of the stoma.

The opening in the retainer plate 10 is inwardly delimited by a bead 28 which is hollow and thereby forms a gas passage duct 30 which is closed to the rear of the retainer plate (that turned downwards in FIGS. 2–3) by the aid of the plastic film 14. Flatus may enter the gas passage duct 30 from the front of the retainer plate 10, which is in open communication with the interior of the bag when the retainer plate with a bag is in place on the patient, through a plurality of gas inlet openings 32. These are evenly distributed over the perimeter of the bead and expediently, but not necessarily, slit-like.

At an arbitrary spot of the retainer plate 10—in FIGS. 2–3 shown at the left side, in FIG. 5 below—there is a recess 34, formed from the rear, to receive a thin, flat deodorizing filter 36. The filter 36 is here of the kind disclosed in EP patent application No. 87 300747.0.

The recess 34 is in open communication with the gas passage duct 30 via a chamber 38. Gases can only leave the gas passage duct 30 and chamber 38 by flowing through the active filter material in the filter 36. The active filter material is surrounded by a plastic film which is firmly connected to and preferably integral with the plastic film 14, which closes both the gas passage duct 30 and the recess 34 to the rear of the retainer plate 10. The only apertures in the plastic film, which is gas- and liquid-tight, is an inlet slit or aperture at one end of the active filter material, turned to the cavity of recess 34; and an outlet slit or aperture at the other end of the filter material, turned to the front of the plastic film 14. These slits are not visible in the drawings because the longitudinal direction of the filter is perpendicular to the plane of the paper (FIGS. 2–3) in the embodiment shown and hence tangential relative to the retainer plate. Here the filter is rectangular but it may even be a circular arc or shaped otherwise. It may also be of another type.

It is seen from FIGS. 2 and 3 that the interspace between the filter 36 at one hand and the adhesive and sealing pad 12, the portion of film 14 covering this part of pad 12 and the microporous tape at the other hand is free, the heat sealing or other joint of adhesive and sealing pad/film only extend radially at little outside the gas passage duct 30.

When the retainer plate with a bag 40 is positioned on the patient around the stoma 20, which in most cases protrudes a little into the bag, flatus flowing from the entrance aperture 44 of the bag and accumulated in its interior may penetrate into the gas passage duct 30 through openings 32 and from there through passage 38 and filter 36 to the outer world if it is an ordinary single bag; or into the interior of an outer bag 46 as shown in FIG. 5. The outer bag 46 is no hindrance for the admission of the deodorized flatus to the outer world since it is not hermetically closed and should not be so.

The only difference between FIGS. 2 and 3 is that the embodiment according to FIG. 3 is provided with a layer of highly absorbent material 47 for catching possible particles of liquid or mixtures of particles of liquid and solids might possibly arrive to the entrance of the active filter material from openings 32 through gas passage duct 30 and passage 38. Such particles might clog the filter and render it inactive.

In the embodiment shown the bag 40 is adapted to be sealingly secured to the coupling means by the aid of an area with a pressure sensitive adhesive 50 which is caused to adhere to a flat area 52 on the front of the coupling means around and up to the radially outer side of bead 28. The diameter of the inlet opening 44 of the bag thus normally corresponds to the outer diameter of bead 28. The pressure-sensitive adhesive is normally most expediently situated on the bag but actually may be situated on retainer plate 10.

Instead of adhesive joining of bag to coupling plate, these two parts may be provided with co-operating coupling rings of essentially known kind adapted for the purpose.

Figure 4:
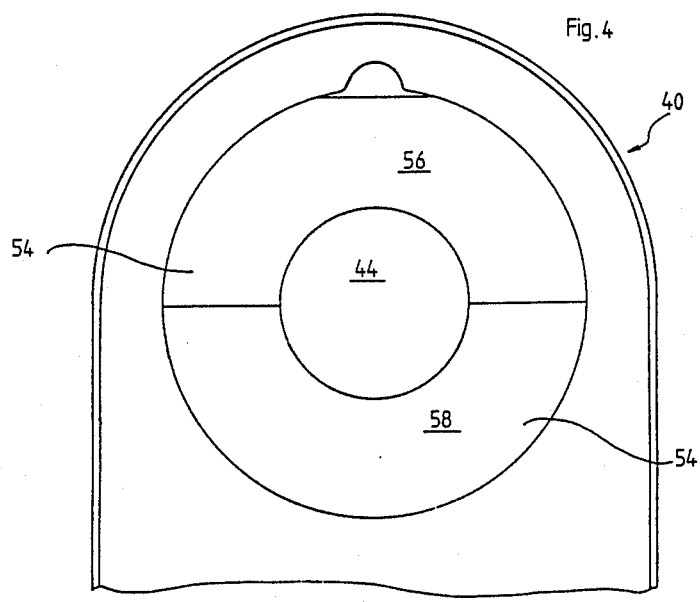
FIG. 4 shows a part, seen from the rear and in smaller scale, of a disposable bag for use in connection with the coupling means shown in FIGS. 1-3.

In FIG. 4 it is seen that the bag 40, which may be of the usual kind for adhesive securing directly or indirectly to the patient, is provided with a bipartite, releasable protective cove 54, e.g. of siliconized paper, covering the entire layer of pressure-sensitive adhesive. This protective cover differs from known bipartite protective covers for ostomy appliances in that the dividing between the two separate parts 56 and 58 is straight, horizontal in the situation of use and diametric.

The advantage of this bipartite protective cover is that when replacing the bag, the coupling means remaining adhered to the skin, the patient may remove one part of the protective cover and bend the corresponding portion of the bag, e.g. the upper portion, a little away from the body of the patient so that the exposed adhesive does not come into contact with the retainer plate. After this the patient may lead the lower portion upwardly towards bead 28 with the other part of the protective cover in contact with the retainer plate until contact has been established between the inner edge of the relevant part of the bag entrance and the bead. Immediately hereafter the portion of the adhesive area freed from the protective cover is bent onto the retainer plate, the other portion is bent a bit outwardly for removing the remainder of the protective cover and is thereafter, adhered. There is obtained in this manner a high degree of security for a correct centering and positioning of the bag on the retainer plate, whereas such correct positioning is difficult when the entire adhesive surface is laid free.

In the foregoing the invention has been substantially only described in connection with a fundamentally ordinary disposable bag for stomatists.

It is, however, equally suitable for use in an ostomy bag system of the kind visualized in FIG. 5, comprising besides a coupling means according to the invention a wc-flushable inner bag 40 and a protecting outer bag 46, both known per se.

The system for affixing the inner bag 40 to the retainer plate 10 is the same whether such a double bag system or an ordinary single bag system as hereinbefore is concerned, even so as regards the bipartite protective cover.

In such a system the inner bag 40 consists of a laminated sheet the outer layer of which is a water soluble film which is also a good gas barrier, e.g. of polyvinyl alcohol, whereas the inner layer is waterproof but mechanically weak so that it becomes disintegrated by the turbulence while flushing. The particular construction of the retainer plate as explained in connection with FIGS. 1-3 assures good safety against leakage and there is therefore little risk of damaging the inner bag during use and hence before intended. Should it nevertheless occur, the outer bag—which is normally used several times—ensures that the damage is limited to precisely the outer bag which is of a mechanically strong, waterproof material. Examples of this are plastics coated textile fabric and comparatively strong, water-tight plastic sheets. The outer bag does not need to be gas-tight because the inner bag has to consist of a gas-tight material.

With the constructions of the coupling plate shown in FIGS. 1-3, the outer bag 46 may be suspended on the rear of the coupling means as shown in FIG. 5, whereby it rests in the upper part of the gap between the retainer plate 10 and the adhesive and sealing pad 12 with the plastic film sitting thereon. The connection need not and should not be gas-tight since deodorized flatus flowing from the filter 36 to the interior of the outer bag 46 must be able to escape.

Figure 6:
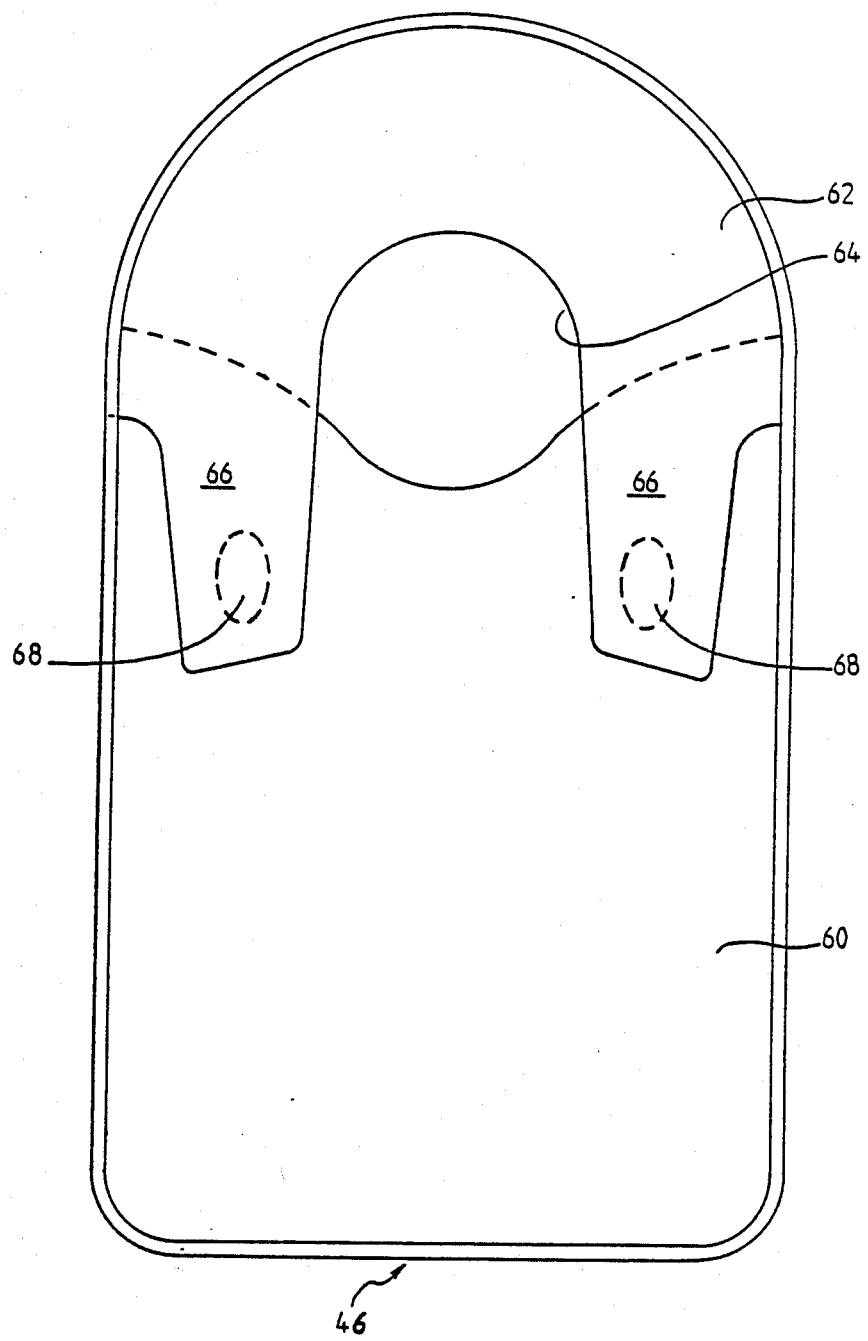
FIG. 6 shows an outer bag for use in the bag system, seen from the rear.

It is particularly convenient if the rear wall of the outer bag be arranged as shown in FIG. 6. It is bipartite with a lower portion 60 which in the position of use extends to the lower part of the area of bonding between retainer plate 10 and adhesive and sealing pad 12, whereas its upper portion is arranged as a plate-like portion 62 having a recess 64 which is open downwardly and surrounded by two flaps 66, and has a contour in its upper part which fits for bearing against the upper half of the gap between the retainer plate 10 and the adhesive and sealing pad 12 (including the film 14). By virtue of this, the outer bag may be easily removed from a filled inner bag thereby that the flaps 66 and the upper portion of the outer bag are bent upwardly and in a direction away from the patient, after which the entire outer bag may be easily pulled downwards, away from the inner bag. When this has been replaced it is correspondingly easy to position the outer bag in place around the new inner bag.

As an extra safety measure the flaps 66 may be provided at the inner side with a Velcro type closure means to co-operate with complementary areas on the outer side of the lower portion of the outer bag, or there may be other closure means such as areas of pressure sensitive adhesive or snap fastener-like means.

I claim:

1. A re-usable coupling means for securing to the body of the patient a flexible disposable bag for collecting intestinal wastes from an ostomy, comprising
   (a) a retainer plate of a comparatively stiff plastic material, provided with an opening adapted to surround the stoma when the coupling means is positioned around it, and having a gas passage duct connected to a filter for deodorizing flatus, and
   (b) a flexible sealing adhesive member adapted to releasably adhere the retainer plate to skin around the stoma and being permanently connected with the retainer plate,
   which comprises the feature that the gas passage duct is situated in an annular projection protruding from the front of the retainer plate around the opening, said duct, when the bag is positioned correctly on the coupling means, at one hand communicating with the interior of the bag by means of a plurality of gas inlet openings, and at the other hand via the filter communicating with at least one gas outlet opening in the coupling means, and
   wherein the outlet opening for discharging gas from the filter is situated in the rear of the retainer plate, the front of the retainer plate in an area surrounding the annular projection being adapted to hold the bag by the aid of a pressure-sensitive adhesive.

2. A re-usable coupling means for securing to the body of a patient a flexible disposable bag for collecting intestinal wastes from an ostomy, comprising
   (a) a retainer plate of a comparatively stiff plastic material, provided with an opening adapted to surround the stoma when the coupling means is positioned around it, and having a gas passage duct connected to a filter for deodorizing flatus, and
   (b) a flexible sealing adhesive member adapted to releasably adhere the retainer plate to skin around the stoma and being permanently connected with the retainer plate.
   which comprises the feature that the gas passage duct is situated in an annular projection protruding from the front of the retainer plate around the opening, said duct, when the bag is positioned correctly on the coupling means, at one hand communicating with the interior of the bag by means of a plurality of gas inlet openings, and at the other hand via the filter communicating with at least one gas outlet opening in the coupling means, and
   wherein
   (i) the gas passage duct is closed to the rear of the retainer plate and situated in a bead protruding form the front of the retainer plate, said bead radially inwardly delimiting the opening of the retainer plate and radially outwardly delimiting an area for receiving an area of the disposable bag provided with a pressure-sensitive adhesive,
   (ii) the gas passage duct communicates by means of a plurality of gas inlet opening, distributed evenly over the perimeter of the bead, with the interior of the bag when the disposable bag is positioned correctly on the retainer plate, and
   (iii) the filter is placed adjacent the rear of the retainer plate such that an inlet opening for gas flowing to the active filter material communicates via a small chamber with the gas passage duct and also such that gas can only flow from the duct through this inlet opening and the active filter material, whereas a discharge path for the gas from the active filter material debouches opposite a part of the adhesive member not secured to the retainer plate.

3. A coupling means according to claim 2, wherein the filter is inserted in a recess made from the rear of the retainer plate, said recess being closed at the rear of the retainer plate except for a gas outlet opening, and communicating with the gas passage duct.

4. A disposable bag for collecting intestinal wastes from an ostomy, said bag having an entrance opening for placing around a stoma to collect the wastes and around that entrance opening an area provided with a pressure-sensitive adhesive for adhering the bag to the front of a retainer plate, said bag comprising in combination (a) the retainer plate being of a comparatively stiff plastic material, provided with an opening adapted to surround the stoma when the coupling means is positioned around it, and having a gas passage duct closed to the rear of the retainer plate and situated in a bead protruding form its front around the opening, the bead radially inwardly delimiting the opening of the retainer plate and radially outwardly an area for receiving the bag area of pressure-sensitive adhesive, the gas passage duct communicating by means of a plurality of gas inlet openings, distributed evenly over the perimeter of the bead, with the interior of the bag when this is positioned correctly on the retainer plate, a flatus deodorizing filter being placed adjacent the rear of the retainer plate such that an admittance opening for gas flowing to its active filter material communicates via a small chamber with the gas passage duct and also such that gas can only flow from the bag in use to the outer world via the duct, through this admittance opening, through the chamber, through the active filter material and leave the retainer plate through a discharge opening for the gas from the active filter material debouching opposite a part of an adhesive member not secured to the retainer plate, and (b) said adhesive member being flexible, sealing and adapted to releasably adhering the retainer plate to the skin around the stoma and being permanently connected with the retainer plate.

5. A disposable bag according to claim 4, comprising a bipartite protective cover wherein the dividing line between the parts of the protective cover is diametrical relative to the entrance opening of the bag and horizontal when being worn by an upright patient.

6. An ostomy bag system comprising in combination (a) a conventional disposable toilet-flushable inner bag made of laminated material comprising a water-soluble outer layer which is substantially impenetrable for flatus and a waterproof, mechanically weak inner layer, (b) a conventional, re-usable outer bag of a waterproof, mechanically strong material, (c) the inner bag having an entrance opening for placing around a stoma to collect intestinal wastes, said inner bag around the entrance opening being provided with a pressure-sensitive adhesive for adhering the bag to the front of a retainer plate of a comparatively stiff plastic material, provided with an opening adapted to surround the stoma when the coupling means is positioned around it, and having a gas passage duct closed to the rear of the retainer plate and situated in a bead protruding from its front around the opening, the bead radially inwardly delimiting the opening of the retainer plate and radially outwardly an area for receiving the bag area of pressure-sensitive adhesive, the gas passage duct communicating by means of a plurality of gas inlet openings, distributed evenly over the perimeter of the bead, with the interior of the bag when this is positioned correctly on the retainer plate, a flatus deodorizing filter being placed adjacent the rear of the retainer plate such that an admittance opening for gas flowing to its active filter material communicates via a small chamber with the gas passage duct and also such that gas can only flow from the bag in use to the outer world via the duct, through this admittance opening, through the chamber, through the active filter material and leave the retainer plate through a discharge opening for the gas from the active filter material debouching opposite a part of an adhesive member not secured to the retainer plate, (d) said adhesive member being flexible, sealing and adapted to releasably adhering the retainer plate to the skin around the stoma and being permanently connected with the retainer plate, and (e) the rear wall of said outer bag being bipartite in such a way that its lower portion extends to a top level which in use borders on the lower part of the area of affixing the sealing adhesive member for the retainer plate, whereas its upper portion is a plate-like portion having a recess extending from its lowermost edge and having a contour in the upper part adapted to engage the upper half of the gap between the retainer plate and the sealing adhesive member, said recess at both sides being delimited by flaps overlapping the lower portion of the rear wall.

7. An ostomy bag system according to claim 6, wherein the flaps on the upper portion of the rear wall of the outer bag and/or the lower portion of the rear wall is provided with means for releasably locking the two portions of the rear wall together.

8. A re-usable coupling means for securing to the body of a patient a flexible disposable bag for collecting intestinal wastes from an ostomy, comprising (a) a retainer plate of a comparatively stiff plastic material, provided with an opening adapted to surround the stoma when the coupling means is positioned around it, and having a gas passage duct connected to a filter for deodorizing flatus, and (b) a flexible sealing adhesive member adapted to releasably adhere the retainer plate to skin around the stoma and being permanently connected with the retainer plate, wherein said retainer plate is a substantially flat circular disc within which the filter is contained and wherein the opening adapted to surround the stoma is substantially centrally placed, the gas passage duct being situated in the retainer disc around said stoma opening and, when the bag is positioned correctly on the coupling means, at one hand communicating with the interior of the bag by means of a plurality of gas inlet openings and at the other hand communicating via the filter with at least one gas outlet opening in the coupling means.

* * * * *